United States Patent
Müller et al.

(10) Patent No.: US 9,498,836 B2
(45) Date of Patent: Nov. 22, 2016

(54) CARRIER WITH A TEST SURFACE WETTABLE WITH LIQUID SOLDER AND METHOD FOR APPLICATION THEREOF

(75) Inventors: Bernd Müller, Falkenberg (DE); Ulrich Wittreich, Velten (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 113 days.

(21) Appl. No.: 14/233,887

(22) PCT Filed: Jun. 22, 2012

(86) PCT No.: PCT/EP2012/062067
§ 371 (c)(1),
(2), (4) Date: May 13, 2014

(87) PCT Pub. No.: WO2013/010748
PCT Pub. Date: Jan. 24, 2013

(65) Prior Publication Data
US 2014/0284374 A1    Sep. 25, 2014

(30) Foreign Application Priority Data
Jul. 19, 2011 (DE) .................. 10 2011 079 407

(51) Int. Cl.
B23K 1/20 (2006.01)
B23K 3/08 (2006.01)
G01N 13/02 (2006.01)

(52) U.S. Cl.
CPC . *B23K 1/20* (2013.01); *B23K 3/08* (2013.01); *G01N 13/02* (2013.01); *H05K 2203/044* (2013.01); *Y10T 428/12222* (2015.01)

(58) Field of Classification Search
CPC ............ B23K 1/20; B23K 3/08; G01N 13/02; Y10T 428/12222
See application file for complete search history.

(56) References Cited

U.S. PATENT DOCUMENTS

| | | | | |
|---|---|---|---|---|
| 4,409,333 A | * | 10/1983 | Tosima | B23K 31/12 228/104 |
| 4,467,638 A | * | 8/1984 | Greenstein | G01N 13/00 228/103 |

(Continued)

FOREIGN PATENT DOCUMENTS

| | | |
|---|---|---|
| CN | 101153837 | 4/2008 |
| DE | 29923733 | 3/2001 |

(Continued)

OTHER PUBLICATIONS

English language of International Search Report for PCT/EP2012/062067, mailed Nov. 14, 2012, 3 pages.

*Primary Examiner* — Devang R Patel
*Assistant Examiner* — Carlos Gamino
(74) *Attorney, Agent, or Firm* — Slayden Grubert Beard PLLC

(57) ABSTRACT

A carrier plate has test areas for the assessment of a selective soldering process. The carrier plate has different zones, which are provided with peripheral borders. The zones are not wettable with solder, while the peripheral borders are wettable. If a selective soldering head is brought up to the reference areas, then, as long as there is no deficiency in quality, the respective peripheral border must be just wetted with solder, whereby an assessment of the selective soldering process is possible. The test plate advantageously makes a simple optical evaluation possible, for example by visual inspection.

16 Claims, 3 Drawing Sheets

(56) References Cited

U.S. PATENT DOCUMENTS

| | | | | |
|---|---|---|---|---|
| 4,529,116 A * | 7/1985 | Gutbier | ............... | B23K 3/0653 |
| | | | | 228/103 |
| 5,001,923 A * | 3/1991 | Schmitt-Thomas | ... | G01N 13/00 |
| | | | | 73/335.14 |
| 5,457,880 A * | 10/1995 | McKinley | ............ | H05K 1/0269 |
| | | | | 228/105 |
| 5,827,951 A * | 10/1998 | Yost | ...................... | B23K 31/02 |
| | | | | 228/103 |
| 5,979,740 A * | 11/1999 | Rooks | .................. | B23K 3/0653 |
| | | | | 228/103 |
| 6,321,591 B1 * | 11/2001 | Breunsbach | ............ | B05B 15/00 |
| | | | | 382/152 |
| 6,581,438 B1 * | 6/2003 | Hall | ...................... | B23K 31/02 |
| | | | | 73/53.01 |
| 6,758,108 B2 * | 7/2004 | Masatoki | ............... | B23K 31/12 |
| | | | | 228/103 |
| 6,888,360 B1 * | 5/2005 | Connell | ............... | H05K 1/0266 |
| | | | | 324/756.07 |
| 8,056,795 B2 * | 11/2011 | Peterson | ................ | B23K 3/082 |
| | | | | 228/33 |
| 2003/0041753 A1 * | 3/2003 | Regner | ............... | B41F 15/0813 |
| | | | | 101/129 |
| 2004/0001140 A1 | 1/2004 | Murayama | | |
| 2006/0019540 A1 * | 1/2006 | Werthman | ............... | G01K 1/14 |
| | | | | 439/488 |
| 2007/0241165 A1 * | 10/2007 | Deram | .................. | B23K 1/203 |
| | | | | 228/101 |

FOREIGN PATENT DOCUMENTS

| | | |
|---|---|---|
| DE | 102006023325 | 11/2007 |
| DE | 102011079407.7 | 7/2011 |
| JP | 2011-137648 | 7/2011 |
| WO | PCT/EP2012/062067 | 6/2012 |

* cited by examiner

CARRIER WITH A TEST SURFACE WETTABLE WITH LIQUID SOLDER AND METHOD FOR APPLICATION THEREOF

CROSS REFERENCE TO RELATED APPLICATIONS

This application is based on and hereby claims priority to International Application No. PCT/EP2012/062067 filed on Jun. 22, 2012 and German Application No. 10 2011 079 407.7 filed on Jul. 19, 2011, the contents of which are hereby incorporated by reference.

BACKGROUND

The invention relates to a carrier with at least one test area that is wettable with liquid solder. The invention also relates to a method for the use of such a carrier in a test method.

A carrier of the type specified at the beginning is described for example in DE 10 2006 023 325 A1. According to the latter, a test plate, which can be printed with solder paste on a test basis, has a test area, which is of a rectangular configuration. This can be soldered with a pattern, which allows conclusions concerning the degree of wettability of the solder paste on the test area. This allows conclusions to be drawn concerning the quality of the solder material. Test plates of the specified type have proven to be successful for obtaining comparatively realistic test results for soldering operations with comparatively low-cost.

SUMMARY

It is therefore one potential object to provide a carrier with at least one test area that is wettable with liquid solder and allows more informative statements to be made about the soldering process. Furthermore, it is a potential object to provide a method for using such a carrier.

The inventors propose a carrier of the type specified at the beginning, in that the at least one test area is configured as an at least partial peripheral border of a two-dimensional reference area, and at the same time this reference area corresponds in at least one dimension to the required wetting area of a selective soldering process to be tested. Furthermore, the reference area is difficult to wet with liquid solder in comparison with the test area. A reference area that is difficult to wet should be understood as meaning properties of the reference area that lead to it being more difficult to wet than the test area. If during the selective soldering process liquid solder is brought up to the reference area, it cannot remain adhering to the reference area because of the more difficult wettability. The situation is different with the test area, which can be wetted well with soldering material in comparison with the reference area. As soon as the liquid solder comes into contact with the test area, it remains adhering to it and solidifies on it after completion of the selective soldering process.

In order to achieve good wettability of the test area, it may be required to treat it in advance with a flux. Since the reference area corresponds to the required wetting area of the selective soldering process to be tested, it is possible by the selective soldering process to be tested to reach precisely this test area with the liquid soldering material, so that the latter wets the test area. Here it is sufficient that the peripheral border of the reference area is only partially present. It consequently forms the delimitation of the reference area. If the test area is provided for example as metallization on a printed circuit board, the reference area is formed of the difficult-to-wet circuit board material itself, the reference area being defined by the test area forming a peripheral border of this reference area. Other parts of the printed circuit board that are likewise difficult to wet do not count as reference area under this definition.

A partial peripheral border may be formed for example by two parallel straight paths of parallel running test areas. The distance between these parallel test areas then corresponds precisely to the radius of the required wetting area, this only being formed in the dimension lying at right angles to the path of the test areas, while at right angles thereto the reference area is not bordered, that is to say is open. This has the advantage that the soldering head for the selective soldering can be moved toward the reference area from that direction in which the reference area is not bordered, that is to say is open.

The proposed carrier advantageously provides a comparatively simple testing device. This can be produced in specific standard sizes for printed circuit boards, so that these carriers can be introduced without any great problem into a production process that is in progress and can be soldered instead of one of the printed circuit boards normally to be soldered. In this way, a random sample can be taken in the process that is in progress, in order to check certain parameters of the selective soldering installation (more on this below). An evaluation of the test result can be advantageously determined in an easy way by visually inspecting the soldering result on the carrier.

According to an advantageous refinement, it is provided that at a uniform distance from the peripheral border there is provided a peripheral surround, which likewise forms a test area. The distance between the peripheral surround and the peripheral border is likewise difficult to wet with liquid solder in comparison with the test areas, so that no solder bridges can form between the peripheral border and the peripheral surround. While the peripheral border forms the border of the reference area, the peripheral surround is, as it were, an outer surround within which both the reference area and the peripheral border lie. This advantageously allows additional test results to be produced. While the peripheral border must be wetted in a smoothly proceeding selective soldering process, since the reference area corresponds exactly to the size of the nominal wetting area of the selective soldering process, the distance between the peripheral border and the peripheral surround is chosen such that the peripheral surround lies outside the tolerance range for the positioning accuracy of the soldering head underneath the carrier. In other words, on no account may the peripheral surround be soldered in a smoothly proceeding process. If solder nevertheless gets onto the peripheral surround, this is an indication that the admissible tolerance range for the selective soldering process has been exceeded. The reason for this may be that the selective soldering head has been positioned imprecisely underneath the carrier or that the liquid soldering material emerging from the selective soldering head does not have the required geometry. In any case, a subsequent search for the fault can be started in order to continue to ensure the required standard of quality.

Another refinement provides that a central test area that does not touch the peripheral border is provided in the middle of the reference area. This central test area is, as it were, the simulation of solder points or solder traces such as are normally provided on conductor tracks. These are to be soldered by the selective soldering process, so that the soldering result can be optically investigated on these solder points or solder traces. Furthermore, these central test areas also have another purpose. If, for example, the process of the selective soldering happens to be disturbed to the extent that the entire peripheral border of a certain reference area is no longer wetted, it would not be evident after the soldering operation has taken place whether this reference area has been addressed at all by the selective soldering head. The fact that a central test area is provided in the middle of the reference area can however rule out the possibility that a certain test zone is not soldered at all. Even if the wetting of the peripheral border does not succeed as a result of a fault of the selective soldering process, it is nevertheless very probable that at least the central test area is wetted with solder. As a result, the possible assessment process is advantageously made more dependable and simplified.

According to another refinement, it is provided that a circular reference area is provided. A circular reference area can be used in both dimensions for evaluating the positioning accuracy of the selective soldering head, since a peripheral bordering of the circular reference area is possible around the entire periphery of the reference area. By circular reference areas, point soldering can therefore be advantageously assessed particularly easily and dependably.

An alternative refinement provides that an elongated, reference area is provided, the width of which corresponds to the radius of the required wetting area of a selective soldering process to be tested and which has the peripheral border at least on the longitudinal sides. In this case, the longitudinal sides that have the peripheral border lie precisely at right angles to the dimension (direction) that is to be taken into consideration in the selective soldering process with regard to the positioning accuracy. The other dimension preferably does not have any peripheral border, so that the selective soldering head can be made to traverse in the direction of the elongated extent of the reference area, that is to say parallel to the longitudinal sides.

The selective soldering head is preferably made to traverse in an x direction and in a y direction running perpendicularly thereto, whereby, in the case of a printed circuit board for example, all points can be addressed. In the testing of the selective soldering process, the positioning accuracy respectively in the x direction and in the y direction is therefore of particular importance. A simple test can be carried out here by suitable alignment of elongated reference areas. Preferably, the selective soldering head is respectively moved in the x direction or in the y direction, while the liquid solder is passed through between the respective peripheral border forming the longitudinal sides, and thereby wets the reference area. The quality of the selective soldering operation can then be concluded from the wetting result of the peripheral border, and a peripheral surround possibly lying on the outside of the peripheral border.

Furthermore, it may be provided that multiple elongated reference areas are provided, with respectively different alignments in relation to one another, in particular at right angles to one another. As already mentioned, the typical traversing directions of the selective soldering head in the x direction and y direction can be detected in this way. The fact that multiple elongated reference areas are present means that it is also possible above all to try out on a test basis different patterns of movement of the selective soldering head on a carrier. This may for example involve traveling over solder traces in the x and y directions. Furthermore, individual solder points may be addressed. Furthermore, the individual solder points and the solder traces can be addressed from opposite directions, in order to check whether the positioning accuracy is equal in all directions. This also allows the determination of tolerance deviations as a result of a reversal error, that is to say as a result of a reversal of the movement of the soldering head by 180°, in the respective axis. Altogether, the soldering results may be evaluated by the user with knowledge of the past movement profile of the selective soldering head.

It is also advantageous if multiple reference areas are provided for wetting areas, with respectively different radii. This has the effect of producing a standardized carrier that can be used in the case of different selective soldering processes. Which of the wetting areas of different radii is used then depends on the geometrical circumstances of the selective soldering head that is used. Reference areas with a radius that is in fact too large can also be used in order to make statements about the positioning accuracy in the case of selective soldering heads with a wetting area that has a smaller radius.

It is also advantageous if the carrier is configured as a carrier plate with an upper side and an underside, the at least one test area being provided on the underside. Such a carrier resembles the customary printed circuit boards that are used as standard for constructing electronic assemblies. With the underside downward, such a carrier plate can be readily introduced into a soldering process for selective soldering and soldered in accordance with the applicable regulations. After removing the carrier plate from the selective soldering installation, the soldering result can be assessed.

It is also advantageous if the carrier plate is connected to at least one through-hole, which is closed on the front side by an indicator for flux. This has the effect of making the through-hole into, as it were, a blind hole, which is downwardly open. This provides a wetting process by flux, which in the case of selective soldering installations is usually applied locally, for example through nozzles. In addition to the soldering process, the wetting with fluxes can also be qualitatively checked by the carrier plate developed in this way. The flux wetting process is considered to have the requisite positioning accuracy if the flux head concerned hits the through-hole and in this way the indicator is wetted with flux. If the flux head misses, the indicator on the other side of the through-hole is not wetted, which is noticeable when it is subsequently examined. An indicator paper may be used for example as the indicator.

According to a particular refinement, multiple through-holes may also be provided, preferably having different hole widths. Here too it is possible, as already mentioned in connection with the selective soldering head, that the through-holes are addressed by the flux head from different directions, so that expanded statements are possible with regard to the achievable tolerances when applying the flux. In particular, it is also possible in the case of through-holes with different hole widths to make out different tolerance ranges. If only the larger through-holes are hit, while the small ones are no longer hit, this allows direct statements to be made concerning the achievable positioning accuracy.

In addition, it may be advantageously provided that the carrier has a temperature indicator, which is sensitive to the temperatures occurring during the selective soldering and the indicator reaction of which is irreversible. A sensitivity in the temperature range of the selective soldering ensures that an indicator reaction is initiated whenever the required temperature range is also reached during the selective soldering. The fact that the indicator reaction is irreversible means that it can also still be ascertained after the carrier has cooled down again after completion of the selective soldering operation. As a result, additional statements are possible, for example an unsatisfactory soldering result may also be due to unfavorable temperature control during the soldering process.

In addition, it may also be provided that the carrier has markings for positioning in an installation for selective soldering. As a result, the positioning of the carrier in the selective soldering installation is facilitated. For example, an automatic optical detection system may be used for the positioning. The more accurately the carrier can be positioned in the selective soldering installation, the more meaningful too are the results of the soldering with regard to the achievability of certain tolerances, since the measuring uncertainties caused by inaccurate positioning of the selective soldering installation can be largely eliminated.

The inventors also propose a method of the type mentioned at the beginning, in that a carrier such as that described above is positioned in the installation. At least some of the reference areas, preferably those that are designed on the basis of their geometry for the selective soldering head concerned, are then selectively soldered. Finally, the carrier is removed from the installation and the soldering result is checked. This may be performed for example by a visual inspection by an experienced user of the selective soldering installation. It is also possible to perform the evaluation in an automated manner, in that for example a digital image of the soldering result is generated and this is subjected to image processing. This can for example detect performed soldering operations and derive from them a quality statement with regard to the selective soldering process.

The proposed method for testing the installation for selective soldering has the advantages already described. In particular, there is an advantage in that the carrier can be easily integrated in a production process that is in progress, in that it is passed through the soldering installation as a substitute for a carrier plate that is in fact to be soldered for an electronic assembly. Furthermore, statements concerning the quality of the selective soldering process are possible in a comparatively easy way. In particular if the process parameters are correct such that the result does not necessitate any objections, the test method can be advantageously concluded very quickly. If, however, soldering defects occur, the cause for this must be investigated. For this purpose, under some circumstances further-reaching test methods are necessary, which however only have to be initiated if the soldering result does not conform to the expected standard of quality.

According to an advantageous refinement of the method, it is provided that, before the selective soldering, a selective flux application to the test areas is performed and the indicator for the fluxes is subjected to flux through the through-holes. On the one hand, the flux application to the test areas has the effect of increasing their wettability, as also required in the case of the selective soldering processes that are normally operated in the selective soldering installation. Furthermore, by subjecting the through-holes to the flux, it can be tested whether the process of the flux application meets the required standard. In this way, additional statements with regard to the quality of the selective soldering process are advantageously possible.

Furthermore, it is advantageous if the reference areas are addressed by a soldering head of the installation from different directions. This makes it possible to determine the tolerance deviations, depending on the parameters of the selective soldering process. It has already been mentioned that in this way it is possible inter alia also to determine the reversal error of a respective x axis or y axis, that is to say tolerance deviations that arise in dependence on the direction of movement of the selective soldering head during the selective soldering.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
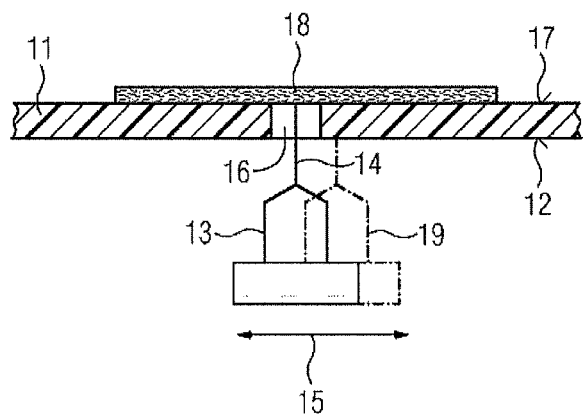
FIGS. 1 to 3 schematically show selected elements of an exemplary embodiment of the proposed method for testing and FIGS. 4 and 5 show the respective plan view of the front side and the rear side of an exemplary embodiment of the proposed carrier.

Reference will now be made in detail to the preferred embodiments of the present invention, examples of which are illustrated in the accompanying drawings, wherein like reference numerals refer to like elements throughout.

According to FIG. 1, it is shown how a test plate 11 can be subjected to flux 14 from an underside 12 by a flux head 13. The flux head 13 is moved here in the horizontal direction 15, it also being possible for flux to be applied to an indicator 18, located on the upper side 17 of the carrier plate, through a through-hole 16. The indicator is a paper, which lies on the upper side 17 and in the case of wetting with the flux 14 shows a change of color.

It is evident how the through-hole 16 can be used for determining the positioning accuracy of the flux head 13 in the horizontal direction 15. The hole width of the through-hole 16 corresponds in this case to the admissible tolerance range in the positioning of the flux head 13. This is so because, as long as the latter is positioned within the tolerance range defined by the through-hole 16, the jet of flux 14 hits the indicator 18. Dash-dotted lines are used also to indicate an inadmissible position 19, in which the jet of flux hits the underside 12 of the test plate 11 such that the indicator 18 is not wetted with flux. This can be taken into consideration in an evaluation of the test result of the test plate 11.

Figure 2:
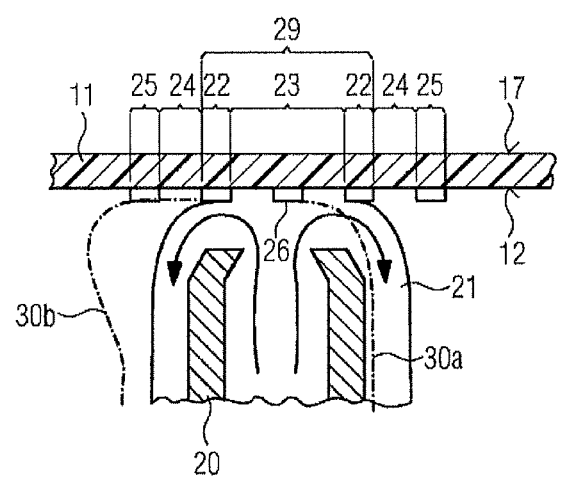

In FIG. 2 it is evident that the underside 12 may also be provided with various test areas, which can be wetted with the liquid solder 21 applied by a solder head 20 for the selective soldering. As the first test area, a peripheral border 22 encloses a reference area 23 that is difficult to wet with solder and lies inside the peripheral border 22. At a distance 24 from the peripheral border 22 there is a peripheral surround 25, which forms a further test area for the wetting with solder. Furthermore, in the center of the reference area 23 there is also a central test area 26.

If the considered dimension of the two-dimensional area (in FIG. 2 this runs in the plane of the drawing), is equal to the radius of the required wetting area, the test area that the peripheral border of the reference area forms is still just touched by the liquid solder material of the selective soldering process, so that there is a wetting of the test area. However, the dimension of the two-dimensional reference area may also be somewhat smaller than the radius of the required wetting area, since of course the peripheral border itself also has a spatial extent. In this way, the test area is advantageously also soldered more dependably. In this case, for example, the reference area including the peripheral border may altogether correspond in the dimension considered to the radius of the required wetting area. In this way, however, a wetting of the test area will also take place when the wetting area of the selective soldering process to be tested turns out to be somewhat too small. In this case, a tolerance range that corresponds precisely to the extent of the peripheral border is defined on the carrier.

Figure 3:
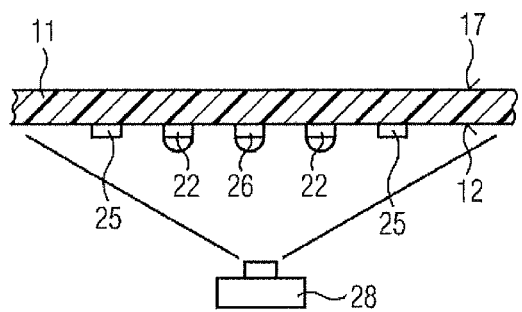

In FIG. 2 it is also evident that the liquid solder 21 wets both the central test area 26 and the peripheral border 22. As can be seen from FIG. 3, therefore, after removal of the soldering head 20 from the underside 12 of the test plate 11, soldered deposits remain on the central test area 26 and the annular peripheral border 22, and these deposits solidify there. Since the process does not involve any quality deficiencies with regard to the tolerances, the likewise annular peripheral surround 25 remains unwetted with solder. This test result can, for example, be recorded and evaluated by a digital camera 28.

However, dash-dotted lines are also used to show two other cases in FIG. 2. The soldering head 20 is intended to provide a wetting area 29, which in the exemplary embodiment lies right on the outside of the peripheral border 22. If, however, not enough solder leaves the soldering head 20, this causes a contour 30a of the solder that lies outside the admissible tolerance range for the wetting area 29 and is therefore too small. Although the central test area 29 is still wetted by the solder, so that it is evident in the test result that the soldering head 20 was brought up to the test areas, the peripheral border 22 remains unwetted. Another case occurs if too much solder leaves the soldering head 20. This causes the contour 30b, so that the diameter of the wetting area 29 becomes too large. As a result, the peripheral surround 29 is also wetted, the distance 24 thereby being bridged. This error is still evident in the test result, since the peripheral surround also forms soldered deposits that are comparable to those represented in FIG. 3.

Figure 4:
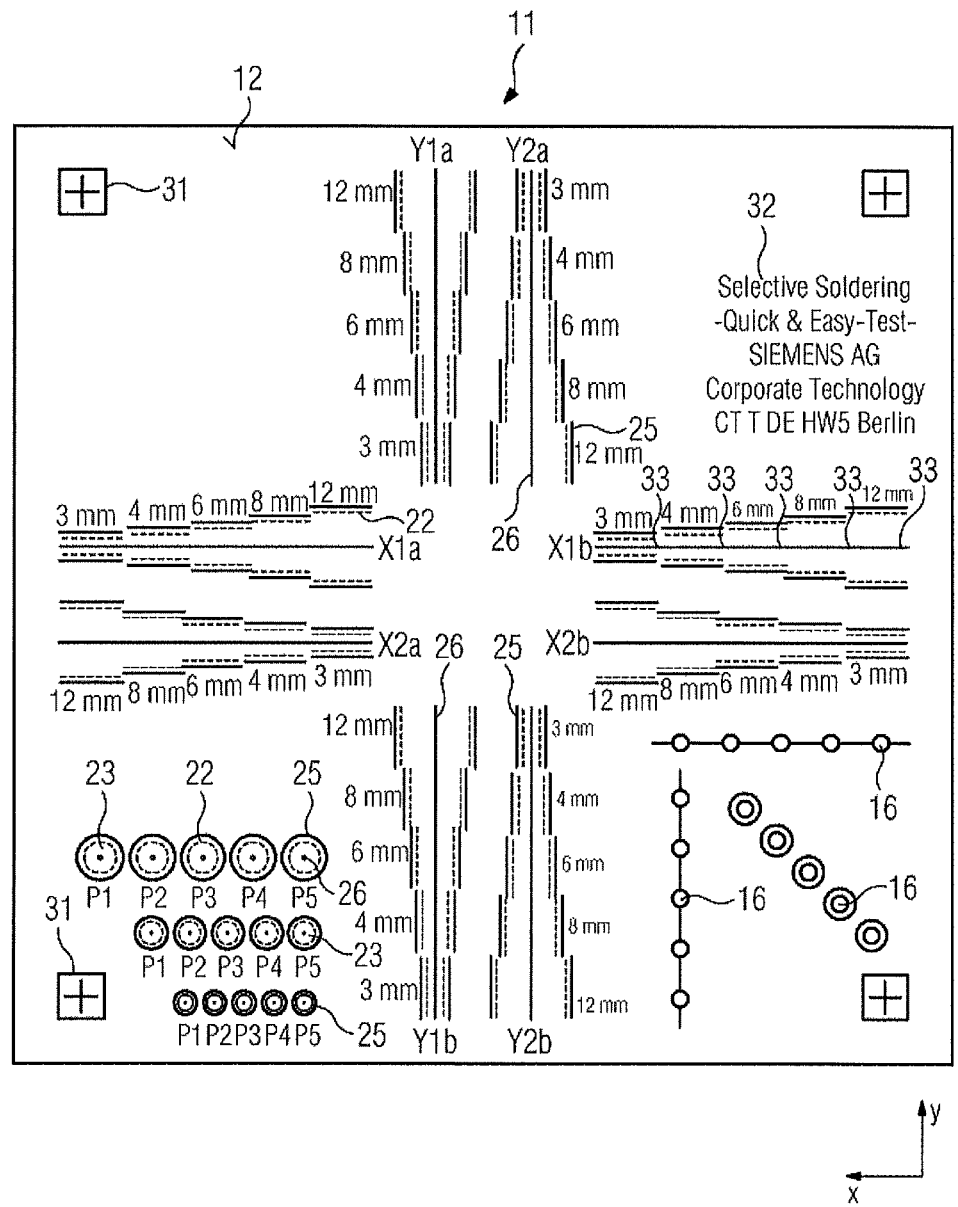

In FIG. 4, an example of a test plate is represented. It shows the underside, which is provided with a pattern of test areas in order to cover different test cases. To be able to position the test plate 11 well in the selective soldering installation, the plate is provided with markings 31. A text field 32, which contains manufacturer and product information, may also be provided. Also shown in the bottom left-hand corner are plan views of round reference areas 23, as already represented in section in FIG. 2. The individual reference areas are also consecutively numbered, to allow an evaluation to be facilitated. The reference areas 23 are intended for being addressed as points by the soldering head. Moreover, reference areas 23 with different diameters are provided, in order to provide a test plate for various soldering head sizes. It is also evident that the peripheral border 22 may also be interrupted, which has the advantage in the case of positioning errors that certain partial regions of the peripheral border 22 are not wetted and, as a result, a conclusion as to the direction in which the positioning error has taken effect is possible.

Also provided on the test plate are elongate reference areas 33, which are respectively defined by a peripheral border 22 along their lengthwise extent. Transversely to their lengthwise extent, however, the reference areas 33 have no peripheral border, so that the soldering head can be passed lengthwise through the reference area.

The reference areas 33 are respectively provided on the test plate with the lengthwise extent in the x direction or in the y direction and are correspondingly labeled with x and y, and moreover are consecutively numbered (also compare the x-y system of coordinates indicated in FIG. 4). In each direction there are multiple reference areas 33 strung out in line with one another, with their widthwise extent staggered for example at 12 mm, 8 mm, 6 mm, 4 mm and 3 mm. This widthwise extent corresponds to that dimension of the respective reference area 33 that is less than or equal to the diameter of the required wetting area of the selective soldering process to be tested. Of each of these staggered reference areas 33 there are multiple staggers on the test plate, so that they can be respectively addressed from different directions, in order to be able to determine the positioning accuracy of the soldering head from different directions, and in particular also a possible reversal error. Apart from the peripheral borders 22, additional central test areas 26 and peripheral surrounds 25 are provided at the reference areas, likewise differing from the form described in relation to FIG. 2 in not having the extent of a point or the extent of a circle but a linear extent, and respectively running parallel to the peripheral border 22. However, a section through the peripheral surround, the peripheral border and the central test area, which runs at right angles to the lengthwise extent thereof, would look just the same as the section according to FIG. 2.

Also evident on the test plate is a series of through-holes 16, which are arranged in line with one another strung out in the x direction, in the y direction and in a diagonal direction. In the test plate represented, these through-holes have the same diameter, but through-holes with different diameters may also be arranged.

Figure 5:
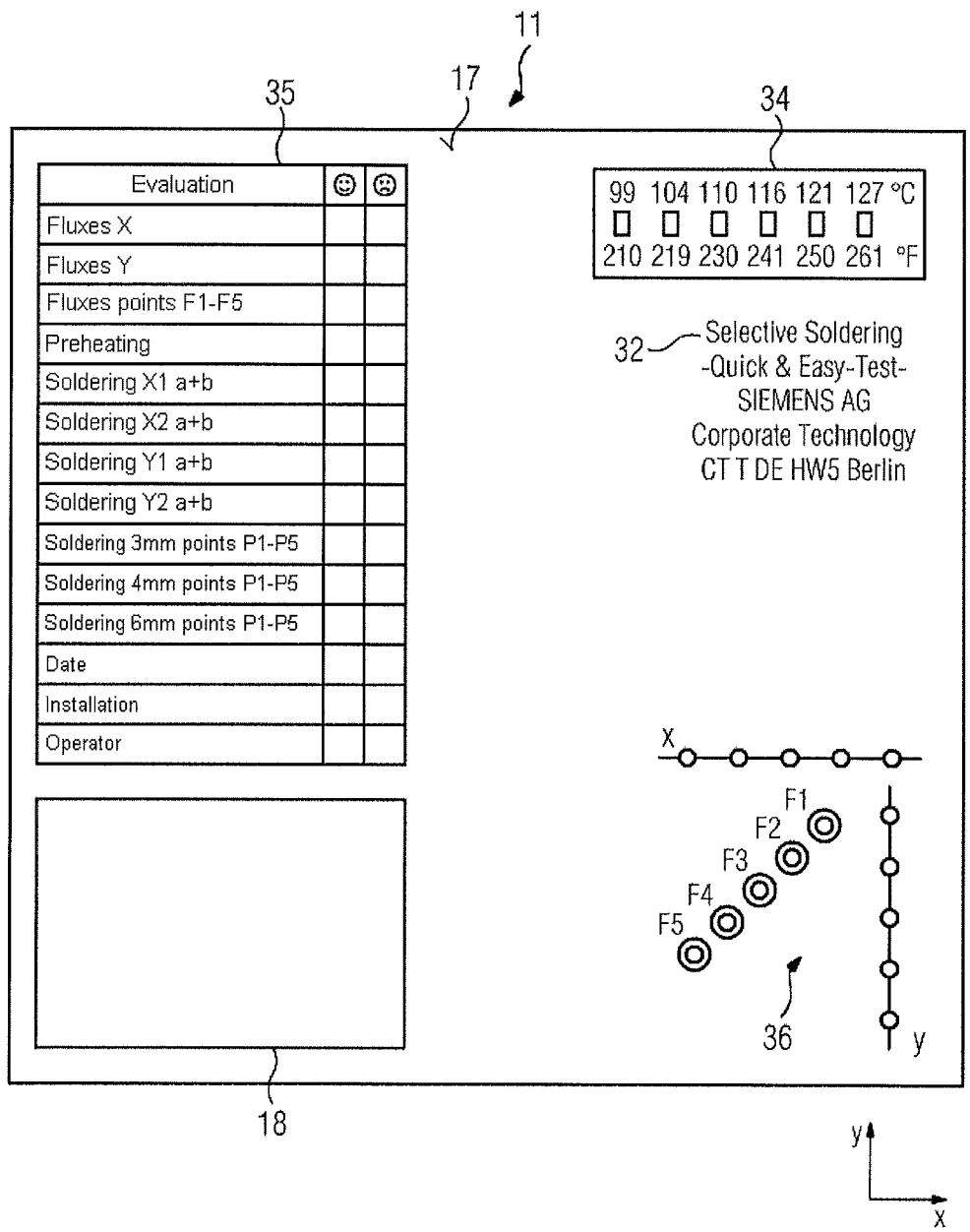

According to FIG. 5, the upper side of the test plate is represented. This additionally has for the evaluation a temperature indicator 34, from which it can be seen from the discolorations what temperature the test plate has reached. There is also a printed table 35, which can be written in after evaluation of the test result, so that the test result can be quickly read off from the test plate. Also shown is the indicator 18, which includes an indicator paper and covers the through-holes (see FIG. 4). Since these holes therefore cannot be seen, the pattern of through-holes 16 according to FIG. 4 is also represented on the upper side of the test plate 11 as an image 36, so that any discolorations on the indicator 18 that indicate wetting with flux can be correctly interpreted.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV,* 69 USPQ2d 1865 (Fed. Cir. 2004).

The invention claimed is:

1. A carrier, comprising:
a plurality of two-dimensional reference areas, each reference area having a central point or central axis and having at least one dimension that is less than or equal to a diameter of a required wetting area of a selective soldering process to be tested on the carrier; and
wherein the plurality of two-dimensional reference areas includes a row of two-dimensional reference areas positioned such that the respective central points or central axes of the two-dimensional reference areas are aligned along a straight line along which a test head is passed; and
a test area corresponding to each two-dimensional reference area in the row of two-dimensional reference areas;
wherein the respective test area corresponding to each respective reference area comprises a pair of separate test area portions on opposing sides of the central point or central axis of the respective reference area and separated from each other by a distance, such that the pair of separate test area portions at least partially enclose the respective reference area;

wherein the distance between the pair of separate test area portions increases progressively from one reference area to the next along the row of reference areas; and wherein each reference area is more difficult to wet with the liquid solder of the selective soldering process than the test area corresponding to that reference area.

2. The carrier as claimed in claim 1, further comprising:
a peripheral surround corresponding to each reference area that forms a second test area at a uniform distance from the partial peripheral border, wherein an area between the peripheral border and the peripheral surround is more difficult to wet with the liquid solder than the test area and the second test area.

3. The carrier as claimed in claim 1, further comprising a central test area corresponding to each reference area that does not touch the at least partial peripheral border is provided in the middle of the reference area.

4. The carrier as claimed in claim 1, wherein at least a portion of the reference areas are circular.

5. The carrier as claimed in claim 1, wherein at least a portion of the reference areas are elongated, a width of the elongated reference area corresponding to a radius of the required wetting area and longitudinal sides of the elongated reference area being defined by the peripheral border.

6. The carrier as claimed in claim 5, wherein multiple elongated reference areas are provided at right angles to one another.

7. The carrier as claimed in claim 1, wherein at least one reference area includes multiple reference areas each provided for one of a plurality of wetting areas having different radii.

8. The carrier as claimed in claim 1, wherein the carrier is configured as a carrier plate with an upper side and an underside, the at least one test area being provided on the underside of the carrier plate.

9. The carrier as claimed in claim 8, wherein the carrier plate is provided with at least one through-hole that is closed on the upper side by an indicator for flux.

10. The carrier as claimed in claim 9, wherein the carrier plate is provided with multiple through-holes having different hole widths.

11. The carrier as claimed in one of the claim 1, further comprising a temperature indicator that is sensitive to temperatures occurring during the selective soldering process and has an irreversible indicator reaction.

12. The carrier as claimed in claim 1, further comprising markings for positioning the carrier in an installation for the selective soldering process.

13. The carrier as claimed in claim 1, further comprising a text field that is configured to be written in.

14. The carrier as claimed in claim 1, wherein each pair of separate test area portions comprises a pair of linear test area segments.

15. The carrier as claimed in claim 1, wherein the plurality of two-dimensional reference areas includes multiple rows of two-dimensional reference areas, wherein the reference areas of each row are positioned such that the respective central points or central axes of the two-dimensional reference areas are aligned along a respective straight line, and wherein the straight lines of the multiple rows extend in different directions.

16. A carrier, comprising:
a row of two-dimensional reference areas, each reference area having a central point or central axis and at least one dimension that is less than or equal to a diameter of a required wetting area of a selective soldering process to be tested on the carrier, wherein the respective central points or central axes of the reference areas are aligned along a straight line;

for each respective reference area in the row of reference areas:
a first test area that is wettable with liquid solder, the first test area comprising a pair of separate test area portions on opposing sides of the central point or central axis of the respective reference area and separated from each other by a distance, such that the pair of separate test area portions at least partially enclose the respective reference area, the respective reference area being more difficult to wet with the liquid solder of the selective soldering process than the first test area; and
a second test area configured as a peripheral surround, the second test area being spaced apart from and at least partially surrounding the first test area, wherein an area between the first and second test areas is more difficult to wet with the liquid solder than the first and second test areas; and wherein the distance between the pair of separate test area portions increases progressively from one reference area to the next along the row of reference areas.

\* \* \* \* \*